United States Patent [19]

Powell

[11] Patent Number: 4,588,821

[45] Date of Patent: May 13, 1986

[54] 2-OXABICYCLO[2.2.1]HEPTAN-6-OL ETHER HERBICIDES

[75] Inventor: James E. Powell, Ripon, Calif.

[73] Assignee: Shell Oil Company, Houston, Tex.

[21] Appl. No.: 621,013

[22] Filed: Jun. 15, 1984

[51] Int. Cl.[4] .......................................... C07D 311/00
[52] U.S. Cl. .................................... 549/397; 549/60;
546/146; 546/174; 546/269; 548/127; 548/128;
548/256; 548/336; 548/374; 548/525; 548/235;
548/203; 548/204; 548/205; 548/247
[58] Field of Search ................ 549/397, 60; 546/269,
546/174, 146; 548/336, 256, 127, 128, 525, 374,
247, 235, 214, 203, 204, 205

[56] References Cited

U.S. PATENT DOCUMENTS 4,542,244 9/1985 Payne et al. .................. 568/825

FOREIGN PATENT DOCUMENTS 81893 6/1983 European Pat. Off. ............ 549/397

*Primary Examiner*—Paul R. Michl
*Assistant Examiner*—Alex H. Walker

[57] ABSTRACT

Compound of the formula

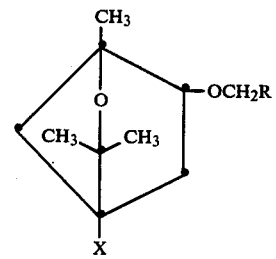

wherein X is —C(O)Hal, —CN, or —C(O)Y in which Y is $OR^1$ or $NR^1R^2$ in which $R^1$ and $R^2$ are H or hydrocarbyl or the like and R are certain optionally substituted hydrocarbyl and heterocyclic groups, are useful as herbicides and plant growth regulators or intermediates thereto. The intermediate 6-hydroxy and 6-oxo-2-oxabicyclo[2.2.1]heptane-4-carbonitriles are also new.

14 Claims, No Drawings

2-OXABICYCLO[2.2.1]HEPTAN-6-OL ETHER HERBICIDES

BACKGROUND OF THE INVENTION

Field of the Invention

The present invention relates to new 2-oxabicyclo[2.2.1]heptan-6-ol ethers, their use as herbicides and plant growth regulators and to compositions containing these new compounds.

SUMMARY OF THE INVENTION

The present invention is directed to novel 1,3,3-trimethyl-4-substituted-2-oxabicyclo[2.2.1]heptan-6-ol ether compounds of the formula 1

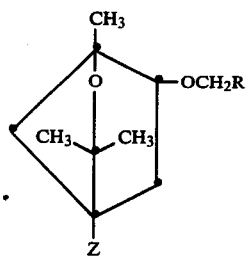

wherein Z is —C(O)Hal in which Hal is a bromine or chlorine atom; —CN; or —C(O)Y in which Y is OR$^1$ or NR$^1$R$^2$ in which R$^1$ and R$^2$ each independently is a hydrogen atom; an alkyl group containing from 1 to 6 carbon atoms; an alkenyl or alkynyl group containing 3 to 4 carbon atoms; an aryl group, aralkyl group or heterocyclic group in which the one or two hetero atoms are N or O, each group containing up to 14 carbon atoms and optionally ring-substituted by one or more halogen atoms or alkyl groups containing 1 to 4 carbon atoms; and R is optionally substituted unsaturated hydrocarbon group containing 2 to 4 carbon atoms, an aromatic group containing up to 14 carbon atoms, a heterocyclic group in which the one or two heteroatoms are each selected from O, S or N and containing up to 14 carbon atoms; a cyano group; a cycloalkenyl group containing 5 to 7 carbon atoms; a cycloalkyl group containing 3 to 10 carbon atoms or a secondary alkyl group containing 3 to 10 carbon atoms; and stereoisomeric forms or mixtures thereof.

Optional substituents for each R include hydroxy; cyano; halogen atoms having an atomic number of from 9 to 35, inclusive; or alkyl, optionally substituted by hydroxy, amino, alkanoylamino, alkoxy or alkylthio; haloalkyl, alkoxy, haloalkoxy, alkylthio, haloalkylthio, alkylsulfinyl, alkylsulfonyl, alkenyl or alkynyl of up to 4 carbon atoms; an aminocarbonyl, carboxyl, amino, or alkanoylamino, each of which hydrogen can be substituted for by alkyl of 1 to 4 carbon atoms; or equivalent kinds of substitutents. Preferably, the optional substituent is an alkyl group containing 1 or 2 carbon atoms, especially a methyl group.

Compounds that possess substantially the same plant growth regulator or herbicidal utility as those described above and can be prepared in like manner are equivalents thereof and include compounds wherein, for example, R is an optionally-substituted, unsaturated hydrocarbyl, cyclohexyl, cycloalkyl, secondary alkyl, mono- or polycyclic aromatic, or saturated or unsaturated heterocyclic moiety or the like, or equivalents thereof, including but not limited to cyano, cyclopropyl, 1-methylcyclopropyl, phenyl, naphthyl, imidazolyl, triazolyl, thiadiazolyl, 2-quinolinyl, 1-isoquinolinyl, pyrrolyl, cyclohexenyl, N-methylimidazolyl, N-methylpyrazolyl, isoxazolyl, oxazolyl, isothiazolyl, thiazolyl, thienyl, 5-methyl-2-furanyl, tetrahydro-2-pyranyl and the like.

The compounds of formula 1, except for when Z is —C(O)Hal, are themselves useful as herbicides and plant growth regulators. When Z is —C(O)Hal the compounds are intermediates to the other compounds of formula 1.

In one embodiment of the compounds of formula 1, Z is —CN or —C(O)Y in which Y is OR$^1$ or NR$^1$R$^2$ in which R$^1$ and R$^2$ each independently is a hydrogen atom or an alkyl group containing 1 to 4 carbon atoms, or R$^1$ is a hydrogen atom and R$^2$ is a phenyl group or a pyridinyl group, substituted or unsubstituted by halogen or alkyl. Preferably, X is —CN, —C(O)NH$_2$ or —C(O)CC$_2$H$_5$.

In another embodiment of the compounds of formula 1, R is an ethynyl group; a phenyl group optionally substituted by one or two halogen atoms of atomic number 9 of 17 or by a methyl group; or a 5- or 6-membered heterocyclic group containing one or two heteroatoms of O or N, optionally substituted by alkyl containing 1 or 2 carbon atoms. Preferably, R is phenyl, 2-methylphenyl or 2-fluorophenyl or tetrahydro-2-pyranyl.

In another embodiment of the compounds of formula 1, Z is —CN or —C(O)NH$_2$ and R is tetrahydro-2-pyranyl, optionally substituted by alkyl, especially by methyl.

The Compounds of the Invention described by formula 1 are prepared by treating the appropriately substituted oxabicycloalkanol with a compound of the formula RCH$_2$X in which X is a halogen atom, such as bromine, chlorine or iodine, or is a hydrocarbylsulfonyloxy group, e.g. mesyloxy, tosyloxy group or the like, preferably in the presence of a strong base and an inert diluent. The strong base is suitably an alkali metal hydride or hydroxide or carbonate, including, for example, sodium hydride, sodium hydroxide, potassium carbonate and the like. Inert diluents are suitably organic solvents, such as ethers, aromatic hydrocarbons, chlorinated hydrocarbons and the like, including, for example, diethyl ether, tetrahydrofuran, dimethyl sulfoxide, toluene, methylene chloride and the like. The reaction is usually carried out under normal pressures and ambient or elevated temperatures. Suitable temperatures for the reaction are from about 0° to about 120° C., preferably from about 20° to about 100° C. The product ethers are recovered and isolated by conventional techniques.

The compounds RCH$_2$X, in which R and X are defined above, are generally known in the art, for example, as in U.S. Pat. No. 3,753,678 and co-pending U.S. Ser. No. 416,572, filed Sept. 13, 1982, as a continuation-in-part of abandoned Ser. No. 331,094, filed Dec. 16, 1981, and the like, and are prepared by conventional procedures known in the art. For example, the tetrahydro-2-pyranylmethanol derivatives R—CH$_2$X in which X is a halogen atom, or hydrocarbylsulfonyloxy group and R is a tetrahydro-2-pyranyl group optionally ring-substituted by one or more alkyl groups are generally known in the art and are readily prepared from the tetrahydro-2-pyranylmethanols, by conventional methods known in the art for preparing halides and sulfonates of alcohols. For example, the tetrahydro-2- pyranylmethanol tosylate is described in R. J. Palmer et al., *J. Amer. Chem. Soc.*, 102 (27) pages 7888–92 (1980) as well as its preparation. The alkyl tetrahydro-2-pyranylmethanols are known materials or can be prepared by literature methods, including application of the methods of G. Buchi and J. E. Powell, *J. Am. Chem. Soc.*, 92, 3126 (1970), E. L. Eliel, M. Manoharan, K. M. Pietrusiewicz, K. D. Hargrave, *Org Magn. Res.*, 21, 94 (1983); E. L. Eliel, K. D. Hargrave, K. M. Pietrusiewicz, M. Manoharan, *J. Am. Chem. Soc.*, 104, 3635 (1982), J. Jurczak and M. Tkacz, *J. Org. Chem.*, 44, 3347 (1979) and the like.

The compounds having the formula 1 wherein Z is CN can be prepared by condensation of 1,4-dibromo-2-methyl-2-butene with an alkyl cyanoacetate or the like in the presence of base, followed by thermolysis of the 2-isopropenyl-1-cyanocyclopropanecarboxylate intermediate to a 3-methyl-1-cyano-3-cyclopentenecarboxylate. Treatment of the cyano ester with a Grignard reagent, methyl magnesium bromide, yields the corresponding 1-(1-hydroxy-1-methylethyl)-3-methyl-3-cyclopentene-1-carbonitrile. This alcohol is epoxidized and cyclized to a 2-oxabicyclo[2.2.1]heptan-6-ol followed by etherification.

Epoxidation/cyclization is conducted by 1) brief refluxing of the cyclopentene methanol with peracetic acid (in chloroform) to give the exobicyclic alcohol, and 2) use of buffered m-CPBA at room temperature to give both "cis and trans" epoxy cyclopentanemethanols followed by treatment of "trans" with tosic acid (in CH$_2$Cl$_2$) to give the exobicyclic alcohol.

The *epoxidation* of the cyclopentene-1-methanol alcohol into the corresponding epoxy-alcohol is effected by action of an oxidizing agent, particularly a peroxide, such as m-chloroperbenzoic acid, peracetic acid or equivalent peroxide reagents. The reaction is conducted at temperatures conveniently in the range of from about $-10°$ C. to about 50° C. or slightly above. Generally, the temperature is from about $-5°$ C. to about 40° C., preferably from about 10° C. to about 30° C. The molar ratio of reactants can vary. Generally, a molar ratio of cyclohex-3-ene-1-ol to oxidizing agent is from about 0.8 to about 1.0. The reaction is usually conducted by forming a mixture of the alcohol and oxidizing agent, preferably while agitating the reaction mixture, e.g. by stirring, and maintaining the desired reaction temperature. The resulting product epoxy-alcohols mixture of cis and trans may be purified or converted without isolation into the 6-exo-hydroxy-2-oxabicyclo[2.2.1]heptane by cyclization as described below.

The *cyclization* (ring closure) step gave a product having the exo-hydroxy configuration in the resulting 2-oxabicyclo[2.2.1]heptan-6-ol. Many acids will catalyze this reaction, but a relatively strong acid such as sulfuric or sulfonic acids are suitable. Preferably, the acid is methanesulfonic acid or an arylsulfonic acid, such as p-toluenesulfonic, benzenesulfonic acids, or the like. Of these, p-toluenesulfonic acid is preferred. The reaction is suitably conducted by adding the acid to the epoxy-alcohol contained in an inert solvent of the type previously described for use in the preparation of the epoxy-alcohol. The reaction is conducted at a temperature conveniently in the range of from about 0° C. to about 50° C. or slightly above. Generally, the temperature is from about 5° C. to about 40° C., preferably from about 10° C. to about 30° C. The molar ratio of reactants can vary. Generally, the molar ratio of acid to epoxy-alcohol is from about 0.01 to about 0.10, and preferably from about 0.02 to about 0.04.

Thus, a 1-cyano-$\alpha,\alpha$,3-trimethyl-3-cyclopentene-1-methanol is converted mainly to 6-exo-hydroxy-4-cyano-1,3,3-trimethyl-2-oxabicyclo[2.2.1]heptane by treating it with an oxidizing agent, such as m-chloroperbenzoic acid, and then a strong acid, such as p-toluenesulfonic acid.

In situations where the endo form is desired, it can be obtained by oxidation of the 2-exo-hydroxy compound to the corresponding ketone followed by reduction of the ketone with sodium borohydride.

The 4-cyano compound (alcohols, ketone or ethers) is converted to the 4-aminocarbonyl compounds (alcohols or ethers) through conventional methods of converting nitriles to amides, e.g. by treatment with a peroxy compound, such as hydrogen peroxide, and strong base, such as alkali metal hydroxide, preferably in the presence of a solvent.

The 4-aminocarbonyl compound is converted to the acid where Z in formula 1 is —C(O)OH by conventional methods using a base, such as potassium hydroxide in the presence of ethylene glycol.

The 4-carboxy compound is converted to (1) the ester where Z is —C(O)OR$^1$ by treatment with an alkanol in the presence of a suitable coupling system, such as dicyclohexylcarbodiimide and 4-dimethylaminopyridine, in the presence of an inert solvent, such as diethyl ether or (2) the acid halide where Z is —C(O)Hal by treatment with, e.g. 1,2-dichloroethane and oxalyl halide.

The ether compounds of formula 1 wherein Z is —C(O)Hal are intermediates to the active compounds of this invention where Z is, e.g. —C(O)Y in which Y is OR$^1$ or NR$^1$R$^2$ in which R$^1$ and R$^2$ are H or alkyl. The conversion of the ether compound where Z is —C(O)Hal to those where Z is —C(O)Y is accomplished by conventional methods known in the art for preparing acids and esters from acid halides, e.g. by hydrolysis or reaction with alcohols, respectively.

Certain of the intermediates to the ether compounds of formula 1 of the invention are novel including the 6-substituted-1,3,3-trimethyl-2-oxabicyclo[2.2.1]heptanes of the formula 2

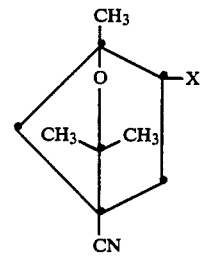

2 wherein X is —OH or =O.

Endo- and exo-oxabicycloalkanol intermediates of formula 2 where X is —OH can be separated by conventional methods, such as crystallization, chromatography and the like, and the geometric forms can be resolved by classical resolution methods to give a substantially pure single isomer.

In situations where the endo form is desired, it can be obtained by oxidation of the 6-exohydroxy compound to the corresponding ketone followed by reduction of the ketone, e.g. with sodium borohydride, L-selectride (LiBH(sec-butyl)$_3$) and the like. 1-Cyano-$\alpha,\alpha$,3-trimethyl-3,4-epoxy-1-cyclopentanemethanol is also novel.

Preparation of this alcohol and the compounds of formula 2 are discussed above.

The materials of formula 1 that have the RCH$_2$O group endo (formula 1b below) are usually more herbicidally active than the exo form (formula 1a below) or the endo-exo mixture and are preferred.

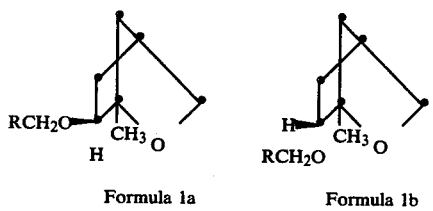

Formula 1a    Formula 1b

These compounds of formula 1a and 1b have the 1S absolute configuration shown above. Such compounds of the formula 1a of the invention are preferred. When an isomer or a mixture of isomers other than a racemic mixture is used substantially free of all other possible isomers, they are usually about 70% pure, although purity above 80% is preferred and a purity above about 95% is highly desireable. This invention contemplates all of the herbicidally active isomers, as well as any mixtures resulting from the synthesis methods used, and deliberately created mixtures.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

EMBODIMENT 1

Methyl 1-cyano-2-(1-methylethenyl)cyclopropane-1-carboxylate

A mixture of 65.3 g of methyl cyanoacetate, 228 g of freshly pulverized potassium carbonate and 800 ml of anhydrous tetrahydrofuran was heated at reflux under nitrogen for 2 hours. A solution of 150.5 g of 1,4-dibromo-2-methyl-2-butene in 500 ml of anhydrous tetrahydrofuran was added slowly dropwise to the refluxing reaction mixture over a period of two days. The solids were removed from the cooled reaction mixture by filtration through a bed of celite. The filtrate was concentrated in vacuo to leave 111.4 g of yellow oil. Distillation of the oil gave 81.3 g of the desired product as a colorless oil: b.p. 95°–105° C. (0.05 mm Hg) consisting of two isomers in a ratio of 2:1 by GLC.

EMBODIMENT 2

Methyl 1-cyano-3-methylcylopent-3-ene-1-carboxylate

A solution of 41.0 g of methyl 1-cyano-2-(1-methylethenyl)cyclopropane-1-carboxylate in 300 ml of toluene was passed through a pyrolysis column packed with glass helices and held at 425° C. A nitrogen flow rate was chosen which resulted in a contact time of 1–2 sec and the pyrolysate was collected in a dry ice-isopropyl alcohol cooled flask. The toluene solution was washed with 300 ml of saturated aqueous sodium bicarbonate and 300 ml of saturated sodium chloride solution, dried (MgSO$_4$), and concentrated in vacuo to leave 32.5 g of brown oil. Distillation of the oil gave 30.4 g of the desired product as a yellow oil: b.p. 75°–100° (0.05 mm Hg).

EMBODIMENT 3

1-(1-Hydroxy-1-methylethyl)-3-methyl-3-cyclopentene-1-carbonitrile

Under nitrogen, a solution of 33.2 g of methyl 1-cyano-3-methylcyanopent-3-ene-1-carboxylate in 300 ml of anhydrous tetrahydrofuran was added dropwise over 30 minutes to a solution of 167 ml of a 3M solution of methylmagnesium bromide in diethyl ether in 200 ml of anhydrous tetrahydrofuran. During the addition, the temperature was controlled at 15° C. by an ice-water bath. After being stirred at room temperature for 16 hours, the reaction mixture was diluted with 1000 ml of diethyl ether and poured into 400 ml of cold, saturated, aqueous ammonium chloride solution. After the phases were separated, the organic layer was washed with 400 ml of water and 400 ml of saturated sodium chloride solution, dried (MgSO$_4$), and concentrated in vacuo to leave 36.7 g of orange oil. Kugelrohr distillation gave 27.7 g of the desired product as an orange oil: b.p. 77° C. (0.02mm Hg).

EMBODIMENT 4

3-(1-Hydroxy-1-methylethyl)-1-methyl-6-oxabicyclo[3.1.0]hexane-3-carbonitrile, (1α,3α,5α)isomer and (1α,3β,5α)isomer To a stirred mixture of 11.65 g of 1-(1-hydroxy-1-methylethyl)-3-methyl-3-cyclopentene-1-carbonitrile in 700 ml of methylene chloride and 210 ml of aqueous sodium bicarbonate was added portionwise at 25°–35° C. 15.3 g of 85% m-chloroperbenzoic acid. After stirring overnight, the phases were separated and the organic phase was washed successively with 200 ml of 1N sodium hydroxide, 200 ml of water and 200 ml of saturated aqueous sodium chloride, dried (MgSO$_4$), and concentrated in vacuo to leave 14.2 g of a colorless oil, as a 1.2;1.0 mixture of diastereomeric epoxides. These diastereomers were separated by flash silica gel column chromatography using 2:8:40 tetrahydrofuran/ethyl acetate/hexane as eluent to give 5.1 g of the less polar (1α,3β,5α) isomer as a colorless oil and using 2:15:33 ratio of the same solvents to give 5.4 g of the more polar (1α,3α,5α)isomer as a colorless oil.

EMBODIMENT 5

6-exo-Hydroxy-1,3,3-trimethyl-2-oxabicyclo[2.2.1]heptane-4-carbonitrile

A solution of 5.30 g of 3-(1-hydroxy-1-methylethyl)-1-methyl-6-oxabicyclo[3.1.0]hexane-3-carbonitrile (1α,-3α,5α) and 0.37 g of anhydrous p-toluenesulfonic acid in 50 ml of chloroform was stirred at room temperature for 48 hours. After dilution with 100 ml of methylene chloride, the solution was washed with 50 ml of 25% aqueous potassium carbonate, 50 ml of water and 50 ml of saturated aqueous sodium chloride, dried (MgSO$_4$), and concentrated in vacuo to provide 4.9 g of the desired product as a cream-colored solid, m.p. 94°–98° C.

EMBODIMENT 6

1,3,3-trimethyl-6-oxo-2-oxabicyclo2.2.1]heptane-4-carbonitrile

A 100 ml roundbottom flask was charged with 50 ml of methylene chloride and 2.4 g of oxalyl chloride. The solution was cooled to −60° C. and a solution of 3.0 g of dimethyl sulfoxide in 6 ml of methylene chloride was added dropwise. The reaction mixture was stirred for 10 minutes at −60° C. and then a solution of 2.90 g of exo-6-hydroxy-1,3,3-trimethyl-2-oxabicyclo[2.2.1]heptane-4-carbonitrile in 3.3 ml of methylene chloride was added dropwise. A white precipitate formed during the addition. The reaction mixture was stirred at −60° C. for 15 minutes and then was allowed to warm to −20° C. Then 8.80 g of triethylamine was added rapidly dropwise by syringe. After stirring for 10 minutes, 50 ml of water was added and the resulting phases were separated. The aqueous phase was extracted twice with 30 ml of methylene chloride and the combined extracts were washed with 60 ml of water and 60 ml of saturated sodium chloride, dried (MgSO4) and concentrated in vacuo to leave 3.07 g of a semi-solid amber residue. This residue was flash chromatographed on silica gel using 4:16:80 tetrahydrofuran/ethyl acetate/hexane as eluent to give two fractions. The first fraction of 1.85 g of cream-colored solid was recrystallized using 1:5-diethyl ether/hexane as a solvent to give 1.13 g of the desired product: m.p. 74°–76° C.

EMBODIMENT 7

6-endo-Hydroxy-1,3,3-trimethyl-2-oxabicyclo[2.2.1]heptane-4-carbonitrile

A 25 ml, three-necked roundbottom flask was flushed with nitrogen, sealed and charged with 7.3 ml of a 1.0M solution of L-selectride (LiBH(sec-butyl)3) in tetrahydrofuran. The solution was cooled to −70° C., becoming opaque white. A solution of 1.10 g of 1,3,3-trimethyl-6-oxo-2-oxabicyclo[2.2.1]heptane-4-carbonitrile in 3 ml of anhydrous tetrahydrofuran was added dropwise. The addition was very exothermic. The reaction mixture was stirred at −70° C. for 1 hour, followed by room temperature for an additional hour. Then, successively were added (a) 0.80 ml of water, (b) 1.60 ml of ethanol, and with ice-bath cooling, (c) 5.88 ml of 10% sodium hydroxide, and (d) 2.49 g of 30% hydrogen peroxide. The reaction mixture was stirred 1 hour at room temperature and then saturated with solid potassium carbonate. The mixture was diluted with 30 ml of 1:1 diethyl ether/tetrahydrofuran solution and 7 ml of water. The phases were separated and the aqueous phase was extracted four times with 30 ml portions of 1:1 tetrahydrofuran/diethyl ether. The combined organic phases were washed twice with 40 ml of saturated sodium chloride, dried (MgSO4) and stripped in vacuo to leave 1.07 g of a cream-colored solid m.p. 68°–83° C. The solid was recrystallized from 1:5 diethyl ether/hexane to give 790 mg of the desired product, m.p. 85°–88° C.

EMBODIMENT 8

1,3,3-Trimethyl-6-endo-(phenylmethoxy)-2-oxabicyclo[2.2.1]heptane-4-carbonitrile A 200 ml three-necked flask was charged with 3.62 g of 50% sodium hydride and 20 ml of dimethylformamide and flushed with nitrogen. A solution of 7.36 of endo-6-hydroxy-1,3,3-trimethyl-2-oxabicyclo[2.2.1]heptane-4-carbonitrile in 40 ml of dimethylformamide was added dropwise while cooling to 25° C. using an ice bath. The resulting grey opaque solution was stirred for 2½ hours, turning green. To this mixture was added dropwise 11.80 g of benzyl bromide in 30 ml of dimethylformamide at 25° C. The reaction mixture was stirred at room temperature overnight. The resulting mixture was quenched with 500 ml of water and extracted thrice with 300 ml of methylene chloride. The combined organic extracts were washed with 300 ml of water and 300 ml of saturated sodium chloride solution, dried (MgOS4) and stripped in vacuo to leave 12.72 g of a damp brown solid. This solid was flashed chromatographed on silica gel using 1.5:3.8 diethyl ether/hexane solvent to give 7.44 g of a cream-colored solid, m.p. 66°–80° C., which was recrystallized using 1:6 diethyl ether/hexane as solvent to yield 5.95 g of the desired product as a white solid, m.p. 84°–88° C.

EMBODIMENT 9

1,3,3-Trimethyl-6-endo-(phenylmethoxy)-2-oxabicyclo[2.2.1]heptane-4-carboxamide

A 25 ml three-necked roundbottom flask was charged with 2.71 g of 1,3,3-trimethyl-6-endo-(phenylmethoxy)-2-oxabicyclo[2.2.1]heptane-4-carbonitrile and 7.5 ml of methylene chloride. This solution was cooled to 0° C. before the sequential addition of 7.5 ml of 30% hydrogen peroxide, 0.697 g of tetrabutylammonium sulfate and 5.0 ml of 20% sodium hydroxide solution. The resulting biphasic mixture was allowed to warm to room temperature and was stirred vigorously for two days. The resulting mixture was diluted with 30 ml of methylene chloride. The separated organic phase was washed twice with 30 ml of saturated sodium chloride solution, dried (MgSO4), and stripped in vacuo to leave 3.36 g of a wet cream-colored solid, m.p. 131°–145° C. This solid was combined with similar material from a second experiment and the combined solids were flashed chromatographed on silica gel using 1:1:2 tetrahydrofuran/ethyl acetate/hexane as solvent to give 3.17 g of a white solid. A 1.78 g portion of this solid was recrystallized using 2:1:~5 diethyl ether/tetrahydrofuran/hexane as solvent to give 1.60 g of the desired product as white crystals, m.p. 151.5°–152° C.

EMBODIMENT 10

1,3,3-trimethyl-6-endo-(phenylmethoxy)-2-oxabicyclo[2.2.1]heptane-4-carboxylic Acid To a mixture of 1.056 g of 1,3,3-trimethyl-6-endo-(phenylmethoxy)-2-oxabicyclo[2.2.1]heptane-4-carboxamide in 40 ml of ethylene glycol were added 6.0 g of freshly pulverized solid potassium hydroxide. The resulting mixture was heated at reflux for seven hours to give a yellow solution. This solution was diluted with 300 ml of water, acidified to pH of 1 with cold 3N hydrochloric acid and extracted thrice with 150 ml portions of methylene chloride. The combined methylene chloride extracts were washed with 150 ml of water and with 150 ml of saturated sodium chloride solution, dried (MgSO4) and stripped in vacuo to leave 1.45 g of a cream-colored solid. This was combined with 1.4 g of similar material from a second experiment and the combined solids were recrystallized using 1:1 diethyl ether/hexane as solvent to give 710 mg of the desired product as a white solid, m.p. 171°–172° C.

EMBODIMENT 11

1,3,3-Trimethyl-6-endo-(phenylmethoxy)-2-oxabicyclo[2.2.1]heptane-4-carbonyl Chloride To a 50 ml roundbottom flask containing 1.15 g of 1,3,3-trimethyl-6-endo-(phenylmethoxy)-2-oxabicyclo[2.2.1]heptane-4-carboxylic acid and 15 ml of 1,2-dichloroethane was added via syringe 0.43 ml of oxalyl chloride. The resulting solution was heated at 55°–60° C. for 3 hours. The solvent was stripped under vacuo to leave the desired product as an orange oil.

EMBODIMENT 12

1,3,3-Trimethyl-N-(4-methylphenyl)-6-endo-(phenylmethoxy)-2-oxabicyclo[2.2.1]heptane-4-carboxamide To a 50 ml three-necked roundbottom flask containing 0.43 g of p-toluidine dissolved in 5 ml of methylene chloride was added via syringe 1.11 ml of triethylamine. To this solution, was added dropwise 1.23 g of 1,3,3-trimethyl-6-endo-(phenylmethoxy)-2-oxabicyclo[2.2.1-]heptane-4-carbonyl chloride (prepared in Embodiment 11 above) at 0° C. The reaction mixture was stirred at room temperature for 2 days. The resulting mixture was diluted with 50 ml of methylene chloride, washed successively with 50 ml of saturated sodium chloride solution, 50 ml of water and 50 ml of saturated sodium chloride solution, dried (MgSO4) and stripped in vacuo to leave 1.55 g of a thick, light brown liquid. This material was crystallized from 1:2 diethyl ether/hexane to give 1.35 g of the desired product as a tan crystalline solid, m.p. 95°–98° C.

EMBODIMENT 13

Ethyl 1,3,3-Trimethyl-6-endo-(phenylmethoxy(-2-oxabicyclo[2.2.1]heptane-4-carboxylate A flask was charged with 2.2 g of 1,3,3-trimethyl-6-endo-(phenylmethoxy)-2-oxabicyclo[2.2.1]heptane-4-carboxylic acid, 20 ml of diethyl ether, 3.49 ml of ethanol, 1.73 g of dicyclohexylcarbodiimide, and 93 mg of 4-dimethylaminopyridine. The acid only partially dissolved in the ether. The reaction mixture was stirred at 25° C. for 40 hours and then diluted with 20 ml of diethyl ether, and the solids were removed by filtration. The filtrate was washed with 20 ml of 0.5N hydrochloric acid, 20 ml of saturated sodium bicarbonate solution and 20 ml of saturated sodium chloride solution, dried (MgSO4) and stripped in vacuo to leave 1.42 g of a wet cream-colored syrup/glass. This material was flashed chromatographed on silica gel using 3:1 hexane/diethyl ether as solvent to yield 0.82 g of the desired product as a thick colorless syrup.

EMBODIMENT 14

1,3,3-Trimethyl-N-(1 methylethyl)-6-endo-(phenylmethoxy)-2-oxabicyclo[2.2.1]heptane-4-carboxamide To a solution of 0.20 ml of isopropylamine and 7 ml of methylene chloride at −10° C. was added via syringe 0.67 ml of triethylamine followed by dropwise addition of 0.74 g of 1,3,3-trimethyl-6-endo-(phenylmethoxy)-2-oxabicyclo[2.2.1]heptane-4-carbonyl chloride. The reaction mixture was stirred at room temperature overnight. The resulting mixture was diluted with 15 ml of methylene chloride, washed successively with 15 ml of 1N hydrochloric acid, 15 ml of saturated sodium bicarbonate solution, 15 ml of water, and 15 ml of saturated sodium chloride solution, dried (MgSO4) and stripped in vacuo to leave 0.72 g of an orange-tan oil. This material was crystallized from cold 5:1 hexane/diethyl ether as solvent. The collected solid melted below room temperature to leave 340 mg of the desired product as a colorless oil.

EMBODIMENT 15

6-endo-(2-Fluorophenylmethoxy)-1,3,3-trimethyl-2-oxabicyclo[2.2.1]heptane-4-carbonitrile Following procedures similar to those described in Embodiment 8 above, the desired product was obtained by treating 6-endo-hydroxy-1,3,3-trimethyl-2-oxabicyclo[2.2.1]heptane-4-carbonitrile with 2-fluorobenzyl bromide.

EMBODIMENT 16

1,3,3-Trimethyl-6-endo-(phenylmethoxy-N-(2-pyridinyl)-2-oxabicyclo[2.2.1]heptane-4-carbonitrile Following procedures similar to those described in Embodiment 12 and 14 above, the desired product was prepared by treating 1,3,3-trimethyl-6-endo-(phenylmethoxy)-2-oxabicyclo[2.2.1]heptane-4-carbonyl chloride with 2-aminopyridine in the presence of triethylamine.

EMBODIMENT 17

1,3,3-Trimethyl-N-phenyl-6-endo-(phenylmethoxy)-2-oxabicyclo[2.2.1]heptane-4-carboxamide Following procedures similar to Embodiment 12 above, the desired product was prepared by treating 1,3,3-trimethyl-6-endo-(phenylmethoxy)-2-oxabicyclo[2.2.1]heptane-4-carbonyl chloride with aniline in the presence of triethylamine.

EMBODIMENT 18

1,3,3-Trimethyl-6-endo-(tetrahydro-2-pyranylmethoxy)-2-oxabicyclo[2.2.1]heptane-4-carbonitrile A 50 ml, three-necked flask was charged with 50% sodium hydride and flushed with nitrogen. A solution of 2.54 g of 6-endo-hydroxy-1,3,3-trimethyl-2-oxabicyclo[2.2.1]heptane-4-carbonitrile in 10 ml of dimethylformamide was added dropwise with stirring at 25° C. The reaction was exothermic and gas evolved. The reaction mixture was stirred for 2½ hours and then 3.0 g of tetrahydro-2-pyranylmethyl mesylate in 5 ml of dimethylformamide was added dropwise. The resulting mixture was stirred at room temperature for two days. An additional 0.4 g of sodium hydride was added and the reaction mixture was stirred for two days. The resulting mixture was quenched with 150 ml of water and extracted thrice with 75 ml of methylene chloride solution. The extract was dried (MgSO4) and stripped in vacuo to give 4.2 g of brown oil. The oil was silica chromatographed using 1:2 ethyl acetate/hexane as eluent and the first fraction was silica chromatographed again using 1:2:1 ethyl acetate/hexane/diethyl ether as eluent. The first fraction was chromatographed yet again on a silica column using 1:1:2 diethyl ether/ethyl acetate/hexane as eluent. The first fraction was recrystallized using diethyl ether/hexane 1:10 as solvent to give 880 mg of the desired product as a white solid, m.p. 58.5°–62° C.

EMBODIMENT 19

1,3,3-Trimethyl-6-endo-(tetrahydro-2-pyranylmethoxy-2-oxabicyclo[2.2.1]heptane-4-carboxamide To a stirred solution of 1.30 g of 1,3,3-trimethyl-6-endo-(tetrahydro-2-pyranylmethoxy-2-oxabicyclo[2.2.1]heptane-4-carbonitrile in 7 ml of methylene chloride were added successively 5.36 g of 30% hydrogen peroxide, 0.32 g of tetrabutylammonium sulfate and 2.35 g of 20% sodium hydroxide. The reaction mixture was stirred overnight at room temperature. An additional 2.0 g of 30% hydrogen peroxide was added and the mixture was stirred overnight. The resulting mixture was diluted with 20 ml of methylene chloride. The separated methylene chloride phase was washed with 15 ml of saturated sodium chloride, dried (MgSO$_4$) and stripped in vacuo to leave 1.46 g of a thick yellow oil that crystallized after sitting at room temperature for a day. The solid was recrystallized from 1:8 ethyl acetate/hexane to give 1.20 g of solid, which was then recrystallized from 1:5 ethyl acetate/hexane to give 1.08 g of the desired product, m.p. 175°–205° C. (with decomposition).

EMBODIMENT 20

Tetrahydro-2-pyranylmethyl Mesylate

A stirred solution of 13.9 g of tetrahydropyran-2-ylmethanol and 18.2 g of triethylamine in 250 ml of methylene chloride was cooled to −10° C. and 15.1 g of methansulfonyl chloride was added dropwise over 5 minutes while maintaining the temperature at −10° C. to 0° C. using a cooling bath. The bath was removed and the mixture was stirred for ½ hour while the temperature reached 16° C. The reaction mixture was washed successively with 150 ml of ice water, 150 ml of 10% hydrochloric acid solution, 150 ml of saturated sodium bicarbonate solution and 150 ml of saturated sodium chloride solution, then dried (MgSO$_4$) and evaporated under vacuum at 50° C. to give 23.7 g of a yellow oil, which was Claisen distilled to yield 19.7 g of the desired product; b.p. 110° C.

The compounds of formula 1 of the Invention other than when Z is —C(O)Hal have been found useful for influencing plant growth and controlling the growth of unwanted plants, being particularly active with respect to grassy weeds and some broadleafed plants. For example, the compounds can change plant morphology; depress the growth of plants, such as broadleafed weeds; inhibit germination; or totally or selectively kill plants depending on the amount used. As herbicides, they appear to be more effective when applied preemergence or pre-plant incorporated (applied to the soil before the seeds have sprouted) than when applied postemergence (applied to the foliage).

At dosages that control unwanted plants (weeds, such as grasses and/or broadleaf weeds), the Compounds of the Invention have shown selectivity to one or more crops, such as cotton, soybeans, sugar beets and wheat.

Protection of a locus or area from undesireable plants is effected by applying a Compound of the Invention, ordinarily a composition of one of the aforementioned types, to the soil in which the plant is growing or in which the seeds are present or to plant and foliage. The Compounds of the Invention, of course, are applied in amounts sufficient to exert the desired action.

For application, the compound of Formula 1 ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula 1.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3-10% by weight of a dispersing agent, 2-15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further soild carrier to give a composition usually containing 0.5-10% by weight of the active compound. Granules are usually prepared to have a size between 10 and 100 BS mesh (1.676-0.152 mm), and may be manufactured by agglomeration of impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluable; certain organic solids or inorganic salts may be disolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3-7% by weight of a blend of surfactants, which act as wetting, dispersing, suspending and binding agents, and 1-3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula 1 as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula 1, ordinarily in a composition of one of the aforementioned types, to soil in which the seeds of the unwanted plants are present, or to the foliage of the unwanted plants.

The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected from 0.1 to 10.0 kg per hectare of the compound of Formula 1 will be satisfactory.

Examples of Activity with Respect to Plants

In the following examples, the species of plants that were tested were:
Barnyardgrass (watercress)—*Echinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnson grass—*Sorghum halepense*
Morningglory—*Ipomoea purpurea* L. (Roth)

Test Procedures

The preemergence (soil) herbicidal activity of compounds of Formula 1 was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of Formula 1 was eveluated by spraying 10-day-old large crabgrass plants, 13-day-old pigweed plants, 6-day-old Johnsongrass plants, 9-day-old velvetleaf plants, 9-day-old yellow foxtail plants and either 9-day-old sicklepod plants or 5-day-old morningglory plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, when the effect of the test compound was evaluated visually, the results being rated on the 0 to 9 scale described above.

Results of the preemergence and postemergence herbicidal activity tests are set forth in Table I.

TABLE I

| | HERBICIDAL ACTIVITY | | | | | | | | | | | | | |
|---|---|---|---|---|---|---|---|---|---|---|---|---|---|---|
| | Preemergence | | | | | | | Postemergence | | | | | | |
| Compound | Barnyardgrass | Garden Cress | Downy Brome | Velvetleaf | Yellow Foxtail | Sicklepod | Morningglory | Crabgrass | Pigweed | Johnsongrass | Velvetleaf | Yellow Foxtail | Sicklepod | Morningglory |
| 15 | 9 | 7 | 9 | 7 | 8 | 7 | — | 6 | 5 | 2 | 6 | 4 | 3 | — |
| 8 | 9 | 8 | 9 | 4 | 8 | 7 | — | 7 | 4 | 4 | 3 | 7 | 2 | — |
| 9 | 9 | 7 | 9 | 7 | 8 | 7 | — | 5 | 4 | 0 | 6 | 2 | 7 | — |
| 10 | 9 | 7 | 7 | 6 | 7 | 7 | — | 7 | 4 | 6 | 3 | 6 | 3 | — |
| 14 | 9 | 7 | 9 | 7 | 8 | — | 7 | 4 | 4 | 2 | 7 | 4 | — | 2 |
| 13 | 9 | 7 | 8 | 7 | 8 | — | 4 | 7 | 7 | 7 | 6 | 7 | — | 4 |
| 17 | 9 | 7 | 9 | 7 | 8 | — | 7 | 6 | 7 | 2 | 5 | 5 | — | 7 |
| 16 | 9 | 7 | 9 | 7 | 8 | 7 | — | 7 | 7 | 0 | 5 | 3 | 7 | — |
| 12 | 9 | 7 | 8 | 6 | 7 | — | 5 | 6 | 6 | 0 | 4 | 3 | — | 6 |
| 18 | 9 | 7 | 9 | 7 | 8 | 6 | — | 0 | 0 | 0 | 0 | 0 | 0 | — |
| 19 | 9 | 7 | 9 | 7 | 9 | — | 4 | 7 | 3 | 4 | 6 | 7 | — | 6 |

— means "no test"

What is claimed is:

1. A compound of the formula

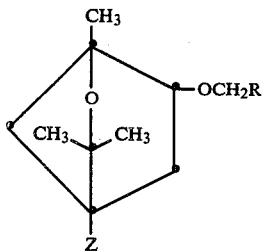

wherein Z is —C(O)Y in which Y is OR$^1$ or NR$^1$R$^2$ in which R$^1$ and R$^2$ each independently is a hydrogen atom, or an alkyl group containing from 1 to 6 carbon atoms; an alkenyl or alkynyl group containing 3 to 4 carbon atoms; an aryl group, aralkyl group or heterocyclic group in which the one or two hetero atoms are N or O, each group containing up to 14 carbon atoms and optionally ring-substituted by one or more halogen atoms or alkyl groups containing 1 to 4 carbon atoms; and R is optionally substituted unsaturated hydrocarbon group containing 2 to 4 carbon atoms, an aromatic group containing up to 14 carbon atoms, heterocyclic group in which the one or two heteroatoms are each selected from O, S or N and containing up to 14 carbon atoms; a cyano group; a cycloalkenyl group containing 5 to 7 carbon atoms; a cycloalkyl group containing 3 to 10 carbon atoms optionally substituted by alkyl of 1 to 3 carbon atoms or a secondary alkyl group containing 3 to 10 carbon atoms; and stereoisomeric form or mixtures thereof.

2. A compound according to claim 1 wherein R is an ethynyl group; a phenyl group optionally substituted by one or two halogen atoms of atomic number 9 or 17 or by a methyl group; or a 5- or 6-membered heterocyclic group containing one or two heteroatoms of O or N optionally substituted by alkyl containing 1 or 2 carbon atoms.

3. A compound according to claim 2 wherein Z is —C(O)Y in which Y is OR$^1$ or NR$^1$R$^2$ in which R$^1$ and R$^2$ each independently is a hydrogen atom, an alkyl group containing 1 to 4 carbon atoms, or R$^1$ is a hydrogen atom and R$^2$ is a phenyl group or a pyridin-2-yl group, each optionally substituted by halogen or alkyl.

4. A compound according to claim 3 wherein R is phenyl, 2-methylphenyl 2-fluorophenyl or tetrahydro-2-pyranyl.

5. A compound according to claim 4 wherein Z is C(O)NH$_2$, or —C(O)OC$_2$H$_5$.

6. A compound according to claim 5 wherein Z is —C(O)NH$_2$ and R is phenyl or tetrahydro-2-pyranyl.

7. A compound according to claim 5 wherein Z is —C(O)OC$_2$H$_5$ and R is phenyl.

8. A compound according to claim 4 wherein Z is —C(O)NH—isopropyl and R is phenyl.

9. A compound according to claim 4 wherein Z is —C(O)OH and R is phenyl.

10. A compound according to claim 4 wherein Z is —C(O)NH—phenyl and R is phenyl.

11. A compound according to claim 4 wherein Z is —C(O)NH—pyridin-2-yl and R is phenyl.

12. A herbicidal or plant growth regulating composition comprising an effective amount of an active compound according to claim 1 and at least one carrier or surface active agent.

13. A method for controlling undesireable plant growth at a locus comprises applying to the locus or the plant an effective amount of an active compound according to claim 1.

14. A method according to claim 13 wherein the control is herbicidal.

* * * * *